US012685488B2

(12) United States Patent
Ramirez-Aristizabal et al.

(10) Patent No.: US 12,685,488 B2
(45) Date of Patent: Jul. 21, 2026

(54) INDEXING PRESENTATION DATA USING BIOMETRIC SENSOR DATA STREAMS

(71) Applicant: Accenture Global Solutions Limited, Dublin (IE)

(72) Inventors: Adolfo Ramirez-Aristizabal, San Francisco, CA (US); Alexandria Emily Pabst, Merced, CA (US); Jordan Alexander Ackerman, San Francisco, CA (US); Edy Liongosari, San Jose, CA (US); Mirjana Spasojevic, Palo Alto, CA (US)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 374 days.

(21) Appl. No.: 18/236,585

(22) Filed: Aug. 22, 2023

(65) Prior Publication Data

US 2025/0064402 A1 Feb. 27, 2025

(51) Int. Cl.
| | |
|---|---|
| *A61B 5/00* | (2006.01) |
| *G06F 3/01* | (2006.01) |
| *G06T 17/00* | (2006.01) |
| *G06V 20/40* | (2022.01) |
| *G06V 40/16* | (2022.01) |

(52) U.S. Cl.
CPC ............... *A61B 5/72* (2013.01); *G06F 3/013* (2013.01); *G06T 17/00* (2013.01); *G06V 20/46* (2022.01); *G06V 40/176* (2022.01)

(58) Field of Classification Search
CPC ........ A61B 5/72; G06V 20/46; G06V 40/176; G06F 3/013; G06T 17/00
See application file for complete search history.

(56) References Cited

U.S. PATENT DOCUMENTS

| | | | | |
|---|---|---|---|---|
| 9,211,077 | B2 * | 12/2015 | Jung | A61B 6/501 |
| 9,521,960 | B2 * | 12/2016 | Lee | H04N 21/42201 |
| 9,886,981 | B2 * | 2/2018 | Pradeep | G06Q 30/0241 |
| 9,891,884 | B1 * | 2/2018 | Baughman | G06V 10/82 |
| 10,179,290 | B2 | 1/2019 | Benedetto | |
| 10,580,018 | B2 * | 3/2020 | Lee | A61B 5/0006 |

(Continued)

FOREIGN PATENT DOCUMENTS

| | | |
|---|---|---|
| JP | 6646319 | 2/2020 |
| JP | 6929380 | 9/2021 |

*Primary Examiner* — Shirley X Jian
(74) *Attorney, Agent, or Firm* — Mannava & Kang, P.C.

(57) ABSTRACT

Methods, systems, and apparatus, including computer programs encoded on computer storage media, for providing a presentation based on stored user experience data. In one aspect, a method includes receiving a data stream including a plurality of biometric data points that each correspond to a particular timestamp in a plurality of timestamps; determining, for a particular timestamp, that a particular biometric data point in the data stream satisfies a predetermined biometric response threshold; in response to determining that the particular biometric data point satisfies the predetermined biometric response threshold, identifying a time period spanning an interval before the particular timestamp through an interval after the particular timestamp; storing user experience data for the identified time period in a storage device; and providing a presentation based on the stored user experience data.

20 Claims, 7 Drawing Sheets

(56)  References Cited

U.S. PATENT DOCUMENTS

| | | | | |
|---|---|---|---|---|
| 10,835,823 | B2 * | 11/2020 | Sumant | G06V 40/174 |
| 11,205,408 | B2 * | 12/2021 | Grace | H04L 67/04 |
| 11,247,021 | B2 * | 2/2022 | Levenberg | G06V 40/171 |
| 11,250,447 | B2 * | 2/2022 | Lee | A61B 5/0205 |
| 11,481,788 | B2 * | 10/2022 | Pradeep | G06Q 30/0202 |
| 11,996,179 | B2 * | 5/2024 | Day | G06V 40/70 |
| 2011/0077548 | A1 * | 3/2011 | Torch | A61B 5/165 |
| | | | | 600/558 |
| 2014/0108842 | A1 * | 4/2014 | Frank | G06F 1/3212 |
| | | | | 713/323 |
| 2015/0313530 | A1 * | 11/2015 | Kodra | G06V 20/41 |
| | | | | 382/203 |
| 2016/0015307 | A1 * | 1/2016 | Kothuri | A61B 5/167 |
| | | | | 702/19 |
| 2017/0246544 | A1 | 8/2017 | Agarwal et al. | |
| 2017/0295402 | A1 * | 10/2017 | Courouge | H04N 21/4532 |
| 2020/0188629 | A1 * | 6/2020 | Levenberg | A61N 1/3603 |
| 2020/0206631 | A1 * | 7/2020 | Sumant | A63F 13/55 |
| 2020/0243055 | A1 * | 7/2020 | Grace | H04L 67/131 |
| 2020/0373001 | A1 * | 11/2020 | Harrison | G06Q 30/0631 |
| 2021/0004574 | A1 * | 1/2021 | Chen | G06V 20/49 |
| 2021/0005224 | A1 * | 1/2021 | Rothschild | H04N 9/8205 |
| 2023/0259551 | A1 * | 8/2023 | Boulard | G06F 16/636 |
| | | | | 700/94 |
| 2025/0064402 | A1 * | 2/2025 | Ramirez-Aristizabal | |
| | | | | G06V 40/176 |

* cited by examiner

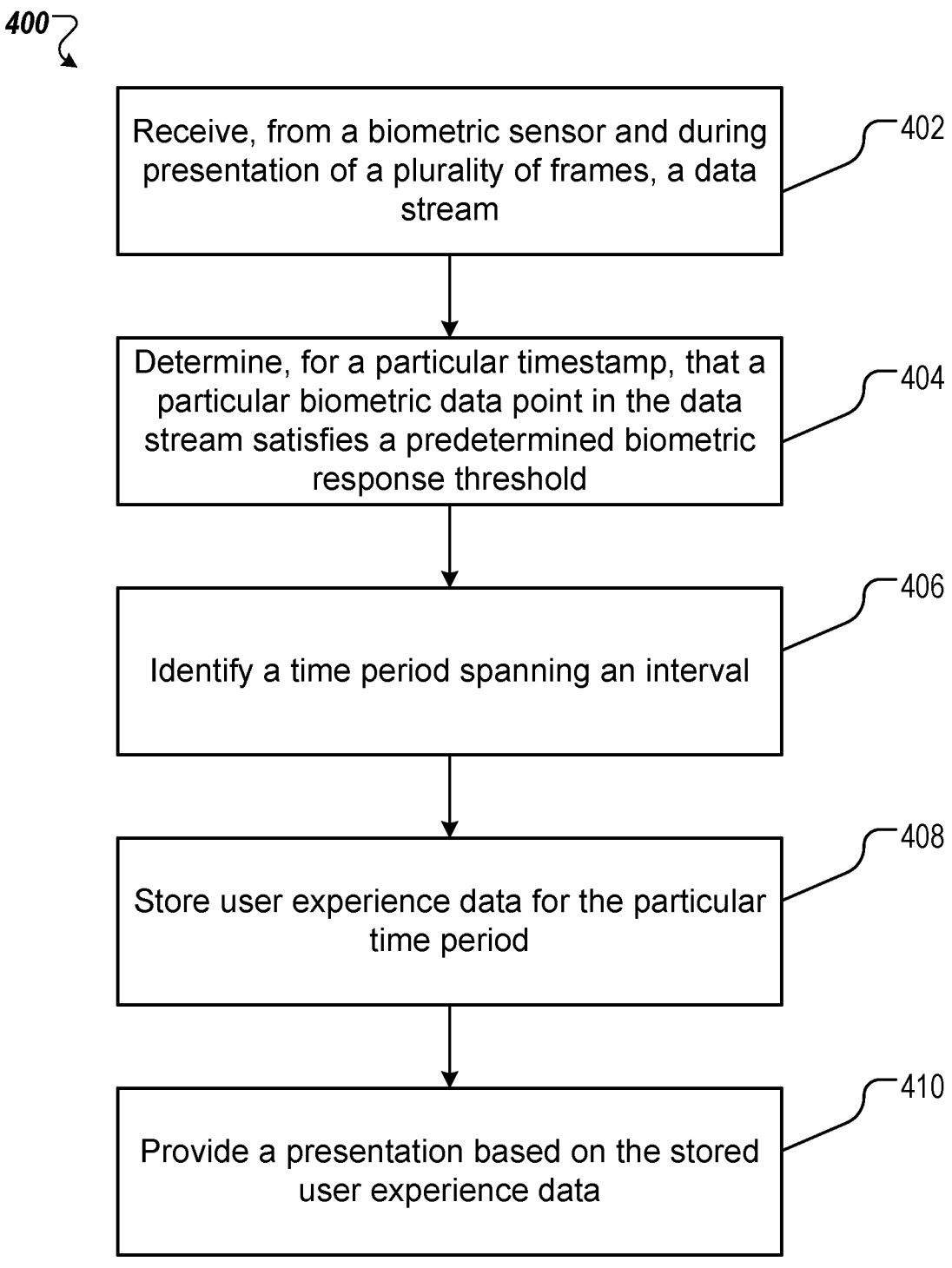

400

Receive, from a biometric sensor and during presentation of a plurality of frames, a data stream ⟶ 402

Determine, for a particular timestamp, that a particular biometric data point in the data stream satisfies a predetermined biometric response threshold ⟶ 404

Identify a time period spanning an interval ⟶ 406

Store user experience data for the particular time period ⟶ 408

Provide a presentation based on the stored user experience data ⟶ 410

Maintain data specifying different biometric response thresholds corresponding respectively to different emotional states — 502

Receive from the user a selection of a particular emotional state — 504

Select a biometric response threshold corresponding to particular emotional state — 506

INDEXING PRESENTATION DATA USING BIOMETRIC SENSOR DATA STREAMS

FIELD

This specification generally relates to interactive viewing systems, and, in particular, relates to monitoring biometric data points of a user of an extended reality viewing system.

BACKGROUND

Rapid advances are being made in extended reality devices, such as augmented reality devices, virtual reality devices, mixed reality devices, and/or the like. Some studies indicate that immersive experiences with extended reality devices leverage affordances of natural human perception (e.g., spatial memory, motion, manipulation, feedback, and/or the like) for better comprehension of three-dimensional (3D) visualizations and enhanced creativity.

SUMMARY

This specification generally describes systems and techniques that indexes presentation data based on monitoring and analyzing data streams captured by biometric sensors. For example, a system can present a video clip for display on a wearable computing device to a user and, in the meantime, extract and store interesting or important scenes within the video clip, where "interestingness" or "importance" is determined based on the data streams generated by the biometric sensors and according to analysis of the biometric data points over time.

According to some implementations, a method can include: receiving, from a biometric sensor and during presentation of a plurality of frames, a data stream including a plurality of biometric data points that each correspond to a particular timestamp in a plurality of timestamps and that are associated with the plurality of frames, wherein the plurality of biometric data points represent measurements of a particular physiologic characteristic; determining, for a particular timestamp, that a particular biometric data point in the data stream satisfies a predetermined biometric response threshold; in response to determining that the particular biometric data point satisfies the predetermined biometric response threshold, identifying a time period spanning an interval before the particular timestamp through an interval after the particular timestamp; storing user experience data for the identified time period in a storage device, wherein the user experience data comprises (1) a set of key frames in the plurality of frames corresponding to timestamps in the time period, and (2) a set of key biometric data points corresponding to timestamps in the time period; and providing a presentation based on the stored user experience data.

Other implementations include corresponding computer systems, apparatus, and computer programs recorded on one or more computer storage devices, each configured to perform the actions of the methods.

Implementations can include one or more of the following features. Receiving the data stream can include receiving the data stream while providing the plurality of frames to a user in a display of an augmented reality device, a virtual reality device, or a mixed reality device that is equipped with the biometric sensor.

The presentation of a plurality of frames can include one or more of: two-dimensional video data, three-dimensional video data, or audio data.

The data stream can include one of: a cortisol level data stream, a heartbeat data stream, an eye tracking data stream, or a brain signal data stream.

Determining that the particular biological signal satisfies the predetermined biometric response threshold can include: maintaining data specifying different biometric response thresholds corresponding respectively to different emotional states; receiving from the user a selection of a particular emotional state; and selecting a biometric response threshold corresponding to particular emotional state as the predetermined biometric response threshold.

The predetermined biometric response threshold can include: an upper threshold value of the biometric data point, a lower threshold value of the particular biometric data point, or both.

The user experience data can further include transcripts of the set of key frames.

The user experience data can further include facial gesture data, speech data, or both of the user while presenting the plurality of frames.

Storing the set of key frames in the storage device can include discarding non-key frames in the plurality of frames corresponding to timestamps outside of the time period.

The presentation can include one or both of: the stored user experience data, or a biological heat map of the plurality of biometric data points.

The methods in accordance with the present disclosure can include any combination of the aspects and features described herein. That is, methods in accordance with the present disclosure are not limited to the combinations of aspects and features specifically described herein, but also may include other combinations or subcombinations of the aspects and features provided.

Particular embodiments of the subject matter described in this specification can be implemented to realize one or more of the following advantages. The technology described in this specification allows for automatic identification of key frames within a sequence of frames included in any of a variety of media content items. The described technology can be used to improve overall user experience of by identifying key frames without any manual trigger from a user viewing the media content item. Since the key frames and associated key biometric data are automatically captured without causing any interruption to the user's experience, users no longer have to interrupt their immersion of an experience to capture those key frames, e.g., users can avoid having to pause to take a picture of a scene that they are experiencing and avoid having to manually record a screen or audio.

Unlike existing techniques that depend on focus group or external observers techniques, the technology also enhances user experience evaluation. For example, focus group techniques wait until the user finishes their experience to capture recollections of what the user experienced, while external observers techniques require the setup of external observation environments that either bias the user's experience due to the presence of an observer, or are affected by the limitations of existing computer vision systems. By using the technology described in this specification, however, the key frames and relevant key biometric are stored based on the natural biometric responses of the user in a way that minimizes interruption to the experience and captures the accurate internal states of the user that would otherwise be biased or occluded by existing techniques.

By monitoring and analyzing data stream captured by biometric sensors, this identification is both versatile, which means that it can be adapted to extract different frames according to different definitions of a key frame, and accurate, which means that there is a low likelihood that any key frames are incidentally missed. Moreover, the key frames and associated data storage allows not only efficient access to, but also optimal use of storage spaces of, frames and relevant key biometric data that otherwise would take a significant amount of time to process, identify, and maintain.

Furthermore, the identified key frames can be stored for further processing in a way that increases the value of the media content items, the biometric sensor data, or both in a range of technical applications. For example, the described technology can assist in the development of more advanced extended reality viewing systems that take into account changes in human emotional states to provide more intelligent, emotion-based content modifications or recommendations to enhance viewer experience or other practical usability of those systems in the fields of, e.g., automotive systems, robotics, aerial systems, boating systems, smart area monitoring, and simulation.

The details of one or more implementations of the present disclosure are set forth in the accompanying drawings and the description below. Other features and advantages of the present disclosure will be apparent from the description, drawings, and from the claims.

BRIEF DESCRIPTION OF THE DRAWINGS

FIG. 4 is a flow diagram of an example process for providing a presentation based on stored user experience data.

Like reference numbers and designations in the various drawings indicate like elements.

DETAILED DESCRIPTION

Figure 1:
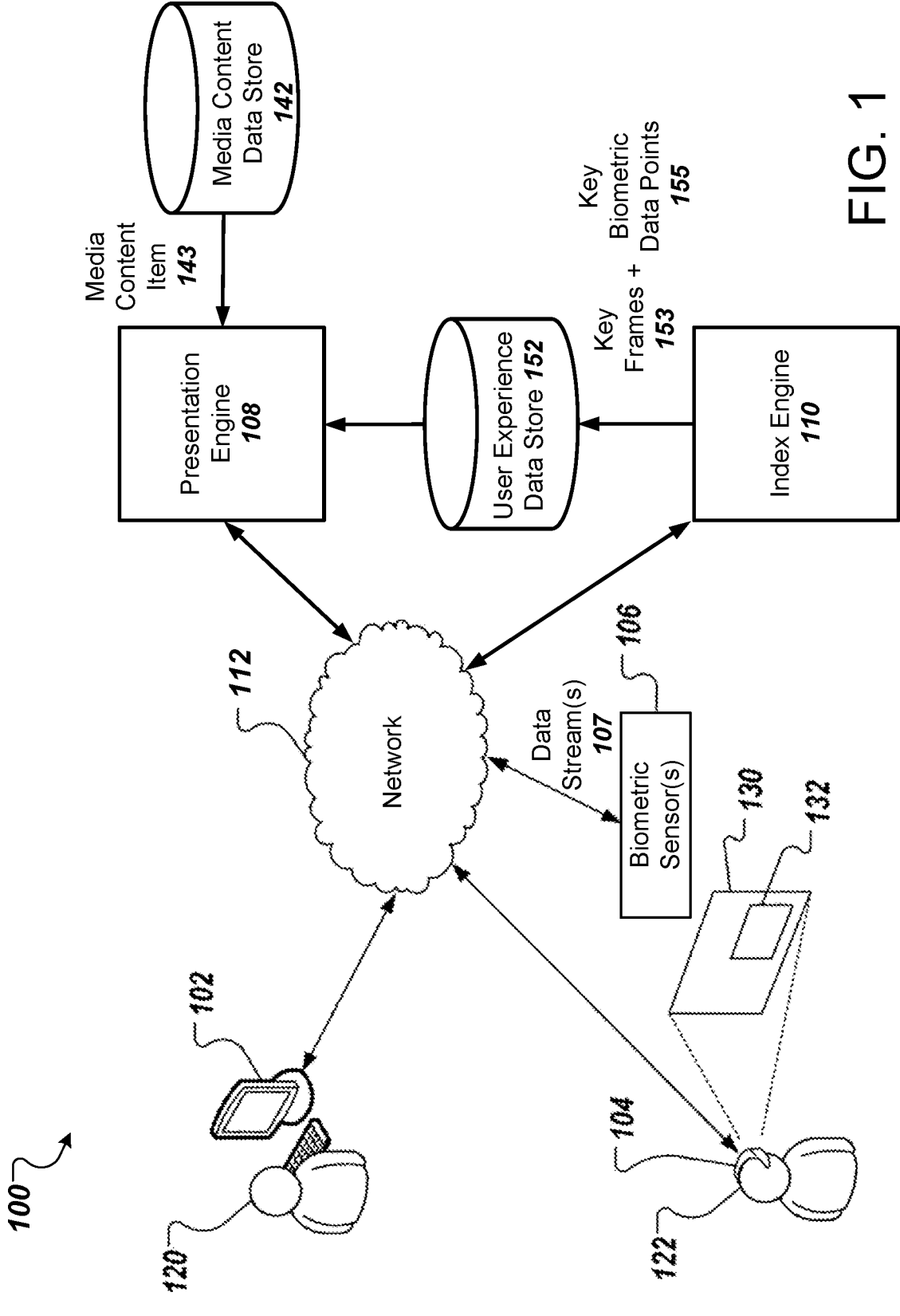
FIG. 1 is a block diagram of an example environment in which media content data can be presented.

FIG. 1 is a block diagram of an example environment 100 in which media content data can be presented. The example environment 100 includes computing devices 102, 104, one or more biometric sensors 106, a presentation engine 108, an index engine 110, a network 112, a media content data store 142, and a user experience data store 152. In some implementations, the network 112 includes a local area network (LAN), wide area network (WAN), the Internet, or a combination thereof, and connects web sites, devices (e.g., the computing device 102, 104), sensors (e.g., the biometric sensors 106), and software systems (e.g., the presentation engine 108 and the index engine 110). In some implementations, the network 112 can be accessed over a wired and/or a wireless communications link. For example, mobile computing devices, such as wearable devices, can utilize a cellular network to access the network 112.

In this specification, the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers. In some implementations, an engine includes one or more processors that can be assigned exclusively to that engine, or shared with other engines.

In some implementations, the presentation engine 108 and the index engine 110 are implemented, e.g., as components of a backend system, within a data center or some other cloud computing system, and are thus remote from the computing devices 102, 104. In other implementations, the presentation engine 108 and the index engine 110 are implemented, e.g., as on-board components of the computing devices, on the local computing and/or memory hardware of the computing devices 102, 104, and are thus physically adjacent to the computing devices 102, 104.

The computing devices 102, 104 can each include any appropriate type of computing device such as a desktop computer, a laptop computer, a handheld computer, a tablet computer, a wearable device, a personal digital assistant (PDA), a cellular telephone, a network appliance, a camera, a smart phone, an enhanced general packet radio service (EGPRS) mobile phone, a media player, a navigation device, an email device, a game console, or an appropriate combination of any two or more of these devices or other data processing devices. As illustrated in FIG. 1, the computing device 102 is provided as a desktop computer, while the computing device 104 is provided as a wearable device. The wearable device can be, for example, a smart watch wearable device, a smart eyewear device, an augmented reality (AR) device, a virtual reality (VR) device, or a mixed reality (MR) device. In other examples, however, the environment 100 can include more or fewer computing devices having the same or different types.

Each computing device 102, 104 includes a respective display device. The display device can be one or more of an internal display device, as in a mobile electronic device or a laptop device or an external display device attached via a display interface. For example, the display device can be a head mounted display (HMD), such as an extended reality display device, for use in augmented reality (AR), virtual reality (VR), or mixed reality (MR) devices.

The computing devices 102, 104 can present media content data within the display devices to respective users 120, 122 of the computing devices. The media content data includes data that makes up a media content item including, for example, movies, television shows, video clips, and/or other forms of single-modal or multi-modal media content. FIG. 1 thus illustrates that the user 122 is viewing a video clip 132 within the display device 130 of the computing device 104. The video clip 132 can include video data (e.g., a still image, a sequence of video frames, etc.), audio data (e.g., recorded speech, music, or other sound), and, in some cases, transcription data (e.g., a speech to text transcription or translation of the audio data).

The media content can be stored in a media content data store 142 that is accessible to the environment 100. The media content data store 142 may be representative of a plurality of data stores 142 as will be appreciated. The presentation engine 108 determines which media content item(s) 143 stored in the media content data store 142 to transmit to the computing device 102, 104 for presentation on the display devices. For example, the presentation engine 108 can select particular media content items on a per-request basis, i.e., in response to requests for media content items made by the users 120, 122 of the computing devices 102, 104. As another example, the presentation engine 108 can select particular media content items on a per-rule basis, i.e., in accordance with a predetermined set of media content presentation rules defined with respect to, e.g., the application(s) that are being executed on the computing devices 102, 104, the location of the computing devices 102, 104, the network coverage availability of the network 112, or the like.

Each media content item 143 has a sequence of frames. That is, each media content item includes a plurality of frames where each frame is part of a plurality of successive frames of media content data that represent the media content item. In the example of a video clip, a frame may be a still image (e.g., a picture), e.g., a two-dimensional (2-D) still image or a three-dimensional (3-D) still image, a moving image, a still image which is part of a moving image, or a moving image including a still image.

The sequence of frames are each associated with a specific timestamp. Each timestamp defines a time point at which the corresponding frame is played relative to other frames of the media content item (e.g., a subsequent frame will usually have a timestamp that is later than the timestamp of a preceding frame in a sequence of frames). For example, the timestamps may be defined relative to a clock. As another example, the timestamps may be defined relative to a presentation timeline of the media content item, where the very first frame is associated with a pre-defined initial timestamp (e.g., timestamp 00:00:00).

The one or more biometric sensors 106 continuously provide biometric sensor information of respective users 120, 122 of the computing devices 102, 104 to the index engine 110 that can be used by the index engine 110 in automated filtering and/or indexing of the frames included in the media content item 143. The biometric sensors 106 can be placed across various appropriate locations within the environment 100 that enable them to capture or collect continuous data streams 107 that include various biometric data points of the users 120, 122. As illustrated in FIG. 1, the biometric sensors 106 are separated from the computing devices. In other implementations, however, the biometric sensors can be coupled to, or included in, the computing devices. In fact, a wearable computing device can have multiple biometric sensors installed thereon.

As used in this specification, the term "biometrics" refers to a measureable physiologic characteristic. A physiologic characteristic can generally be captured in the form of a biometric data point or sample captured by a biometric sensor, which refers to a device configured to acquire such data points. Such devices include, for example, cortisol level sensors (e.g., optical cortisol level sensors), heartbeat sensors, eye motion sensors (e.g., eye tracking sensors), brain signal sensors (e.g., electroencephalography (EEG) sensors), galvanic skin response sensors, temperature sensors, perspiration sensors (or sweat sensors), microphones, video cameras, and other known devices capable of collecting biometric data points.

Each continuous data stream 107 includes a plurality of biometric data points that are captured by a biometric sensor 106 as a function of time. In other words, like the frames included in the media content item, each biometric data point is associated with a specific timestamp. Each timestamp defines a time point at which the corresponding biometric data point is captured by the biometric sensor 106 relative to other biometric data points included in the data stream 107.

The index engine 110 can associate the frames included in the media content item 143 with the biometric data points included in the continuous data stream 107 by synchronizing the timestamps of the frames with those of the biometric data points. For example, the components of the environment 100 can connect to an Internet Protocol (IP) network and run a Network Time Protocol (NTP) daemon to sync time across each other and thus the index engine 100 can determine synchronized timestamps for both media content items 143 and biometric sensor data streams 107.

Actions for automated filtering and/or indexing of the frames can then by performed by the index engine 110 based on analyzing the biometric data points collected by the biometric sensors 106. Specifically, the index engine 110 can continuously receive the biometric data points, i.e., as they become available in a sensor data stream 107, and repeatedly compare them against a set of predetermined biometric response thresholds. The index engine 110 can then use the comparison results to identify a sensor event that triggers the identification of one or more key frames 153 from among all the frames included within the media content item 143.

In some implementations, the index engine 110 can use more sophisticated analysis algorithms, including machine learning algorithms, to analyze the biometric data points, e.g., to recognize certain patterns in these biometric data points, and use the analysis results to identify the sensor event that triggers the identification of key frames 153. For example, the index engine 110 can implement a machine learning model configured as a neural network, a Naive-Bayes model, a decision tree/random forest model, a support vector machine (SVM) model, or the like that classifies EEG signals into one of multiple categories. As another example, the index engine 110 can implement an eye tracking model, such as one that is configured as a convolutional neural network, that measures and determines the eye movements and eye positions of an individual from video data.

In some implementations, the index engine 110 can automatically generate these biometric response thresholds based on biometric tracking, e.g., by using machine learning-based tracking algorithms or by deterministic signal comparisons. For example, this automatic threshold setting can be guided by relative changes across time of biometric data points, which may follow a user's innate biological characteristics. For example, it is known that biometric data points for users naturally have peaks or spikes of activity in response to stimulus presentation such as media content items. These natural spikes of biometric activity are in response to a user's experience and are saliently identifiable in comparison to periods of time when the user is not having a salient response to their environment/media content items presented to them. Accordingly, the biometric response thresholds can be automatically defined by the index engine 110 with respect to the natural salient responses of a user to the media content items presented to them, as biometric activity usually differs relative to when the user is not having a salient response.

Each predetermined biometric response threshold can include one or more numerical values, one or more percentage values, or the like for a corresponding type of biometric data points. In some cases, to be considered as satisfying the threshold, an actual value of a biometric data point needs to be, e.g., less than a predetermined value, equal to a predetermined value, or greater than a predetermined value. Moreover, in fact, each predetermined biometric response threshold can include multiple values, e.g., a lower threshold value and an upper threshold value, that collectively define a range of values. Thus, in those cases, to be considered as satisfying the threshold, an actual value of a biometric data point needs to be not less than (i.e., is greater than or equal to) a lower threshold value and is within the range of values between an upper threshold value and the lower threshold value.

Figure 2:
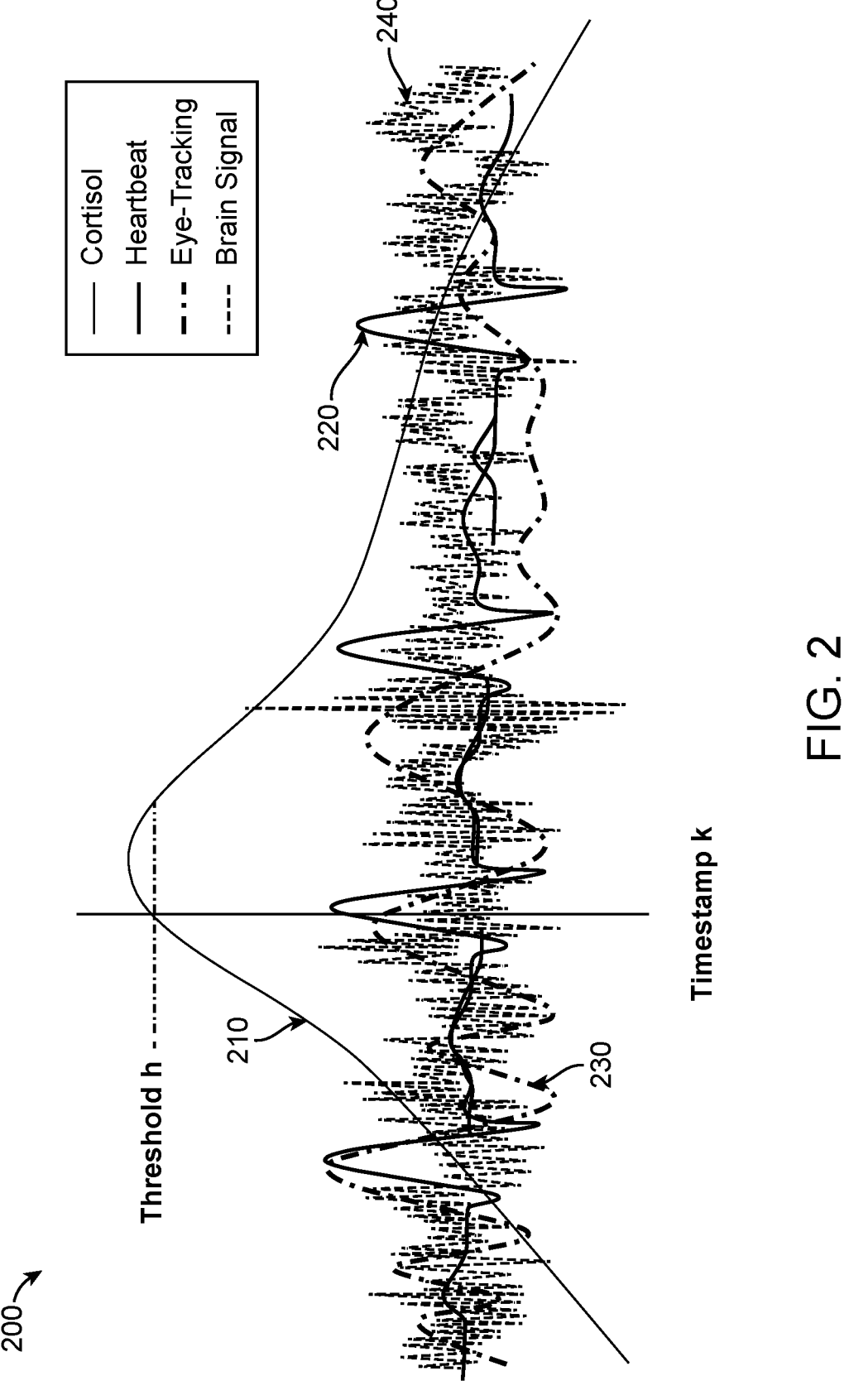
FIG. 2 is an example illustration of biometric sensor data streams.

FIG. 2 is an example illustration of biometric sensor data streams. In the example of FIG. 2, the index engine 110 can monitor the various sensor data streams 210, 220, 230, 240 of a user of a computing device. The sensor data streams include a cortisol level data stream 210, a heartbeat data stream 220, an eye tracking data stream 230, and a brain signal data stream 240. The sensor data streams 210, 220, 230, 240 each include a plurality of biometric data points that are continuously provided by the biometric sensors over the time period during which a media content item, e.g., a video clip that includes a sequence of frames, is presented for display on the display device of the computing device.

Accordingly, in response to determining that a new biometric data point satisfies one or more predetermined biometric response thresholds, a number of frames 153 that are being displayed around a particular time point associated with or identified by the timestamp of the new biometric data point, can be identified by the index engine 110 as "key" frames (while the remaining frames displayed at time points farther away from the particular time point can logically be identified by as "non-key" frames). A copy of the key frames 153 can then be requested by the index engine 110 for storage in a user experience data store 152 that is accessible to the environment 100.

As illustrated in FIG. 2, a biometric data point in the cortisol level data stream 210 that is associated with, e.g., captured at, timestamp k has a value that is greater than or equal to a biometric response threshold h for cortisol level sensor data. Accordingly, the index engine 110 identifies, as a set of key frames, one or more frames from among the sequence of frames included in the video clip that are associated with timestamps in a time period spanning an interval before the timestamp k through an interval after the timestamp k, e.g., a time period that is 0.5 s, 1 s, or 2 s before the timestamp k and 0.5 s, 1 s, or 2 s after the timestamp k. It will be appreciated that any pre-determined time interval can be used, and that the exact interval used may vary depending on the type of response and may also vary in length prior to or after the timestamp k.

Similarly, a number of key biometric data points 155 that are captured by the biometric sensors 106 around the time point associated with or identified by the timestamp of the new biometric data point, can be identified and subsequently requested by the index engine 110 for storage in the user experience data store 152. As illustrated in FIG. 2, the index engine 110 identifies, as a set of key biometric data points that should be stored in the user experience data store 152, biometric data points in the cortisol level data stream 210 that are associated with timestamps in a time period spanning an interval before the timestamp k through an interval after the timestamp k, e.g., a time period that is 0.5 s, 1 s, or 2 s before the timestamp k and 0.5 s, 1 s, or 2 s after the timestamp k.

In some implementations, the exact lengths of these intervals are set by the index engine 110 based on sampling rate, memory storage, or both of the sensor data and possibly other characteristics of the sensor data, so as to achieve optimal usage of storage resources. For example, as will be discussed below with reference to FIG. 6, the interval can be set to be shorter for biometric sensor data that is more data storage intensive and that has a higher sampling rate, while the interval can be set to be longer for biometric sensor data that is less data storage intensive and that has a lower sampling rate.

In a more concrete example, the index engine 110 can set the interval based on a hierarchy of biometric signal resolution and data storage intensity. In this example, given an identified timestamp, a data storage intensive and high sampling rate biometric signal, such as brain signal data points (e.g., EEG signals), can have a shorter interval than biometric signal data points of lower resolution and data storage intensities, such as cortisol level data points or eye tracking data points. Accordingly, the data storage space needed for storing different biometric data points are optimized because storing a large number of biometric sensor data points generated by a biometric sensor with a high sampling rate can be avoided.

In this manner, the media content items 143 that are being presented for display to the users and the biometric sensor data streams 107 that are being generated by using the biometric sensors 106 can be filtered and/or indexed for further processing in a way that enables efficient access to key frames and relevant data that otherwise would take a significant amount of time to process and identify, thereby increasing the value of the media content, the biometric sensor data, or both in a range of technical applications.

The user experience data store 152 can have any suitable data structure, e.g., an array, a stack, a queue, a linked list, a tree, a graph, or the like, that can store these key frames 153, key biometric data points 155, and, optionally, the relationship (e.g., a one-to-one, one-to-many, or many-to-one mapping relationship) between the key frames 153 and the key biometric data points 155. The user experience data store 152 can be implemented in one or more logical or physical storage devices in the environment 100.

In some implementations, as a media content item 143 is being presented for display, the sequence of frames included in the media content item 143 can be temporarily stored in an intermediate buffer to facilitate the subsequent, longer-term storage in the user experience data store 152. After the key frames 153 have been identified from among the sequence of frames (and, analogously, after the key biometric data points 155 have been identified from among the sensor data points) for longer-term, e.g., persistent, storage in the experience data store 152, the temporarily stored data maintained in the intermediate buffer can be discarded. As one example, the intermediate buffer can be in a circular buffer which stores frames that are overwritten with additional frames when a certain length of the stream of frames have been stored (but does not meet any thresholds).

In a simple example, each key frame from a media content item is indexed with the index keys being those key biometric data points (or vice versa, namely each key biometric data point is indexed with the index keys being those key frame). When the goal is to predict possible user reaction to certain media content items, e.g., in response to viewing one or more frames, storing user experience data in this way allows different frames or biometric data points to be efficiently searched for that purpose.

The key frames can be indexed in a more sophisticated way. For example, the key biometric data points can be organized into one or more groupings that represent different human emotional states, and correspondingly the key frames are indexed such that the index keys relate to different emotional states. The emotional states can include neutral, happy, sad, anger, contempt, fear, surprise, confused, stressed, and tender emotions, to name just a few examples. When the goal is to identify user's emotions and/or to take additional actions, e.g., recommend relevant media content to users or modify (e.g., pause, fast-forward, mute, etc.) the ongoing presentation of a media content item, in a way that takes into account changes in human emotional states, storing user experience data in this way allows various frames that correspond to different emotional states to be efficiently searched for that purpose.

Furthermore, actions for generating additional presentation data for presentation to the users 120, 122 can be performed by the presentation engine 108 based on the key frames 153, the key biometric data points 155, or both stored in the user experience data store 152. For example, the presentation engine 108 can generate a visual replay based on the key frames 153 for display on the computing devices 102, 104. For example, the visual replay, which includes the key frames 153 identified from among all the frames included in the media content item 143, can be in the form of a replay of interesting or important scenes within a video clip, where "interestingness" or "importance" is determined based on the data streams generated by the biometric sensors 106 and according to analysis of the biometric data points over time.

As another example, the presentation engine 108 can generate a biological heatmap based on the key biometric data points 155 stored in the user experience data store 152. A heatmap illustrates a graphical representation of the key biometric data points along a given dimension, e.g., a temporal dimension. A heatmap provides a visualization of sensor data point concentrations using a color-coded overview to provide insights into the development of extended reality viewing systems.

Figure 3:
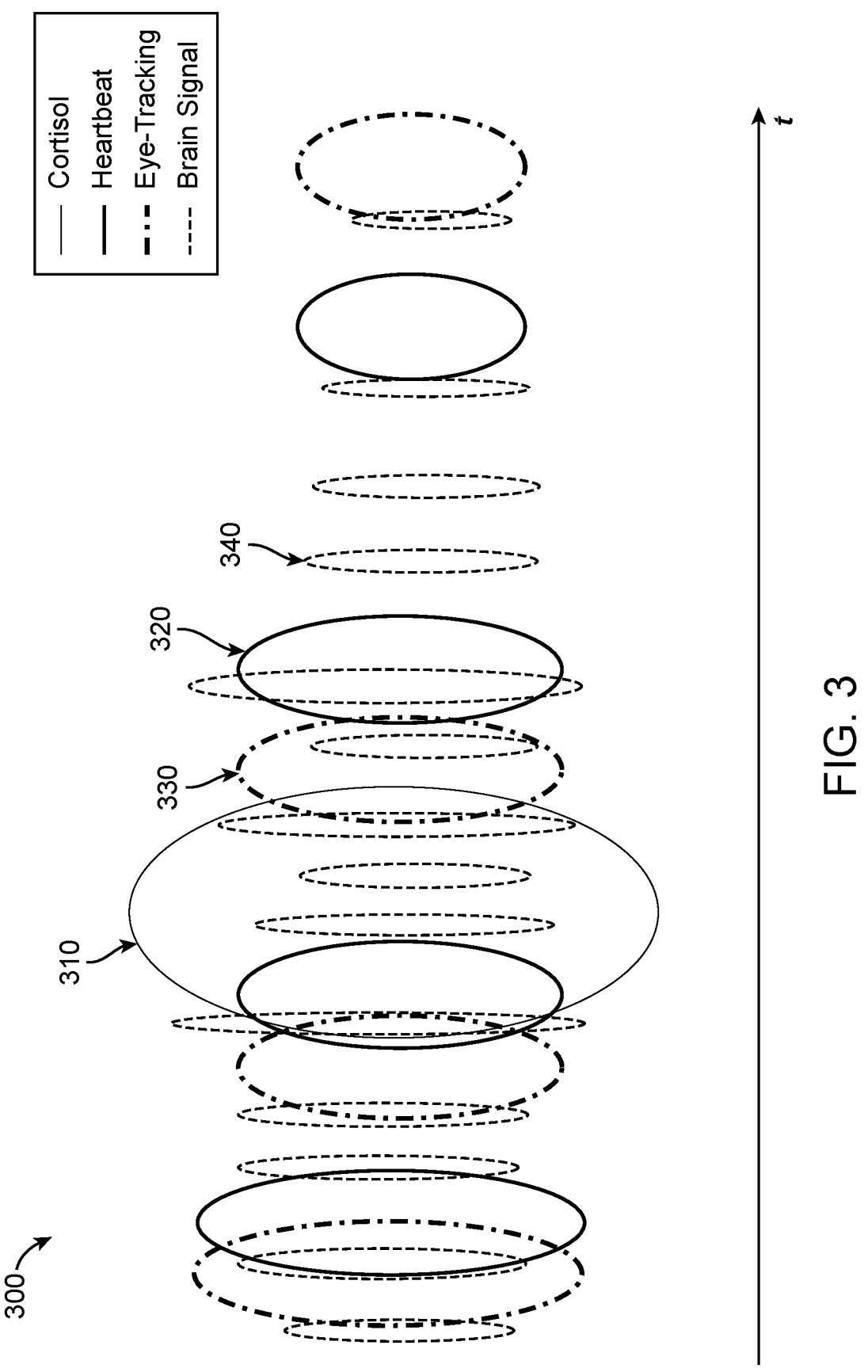
FIG. 3 is an example illustration of a heatmap of biometric data points.

FIG. 3 is an example illustration of a heatmap of biometric data points. In FIG. 3, cortisol level data points 310, heartbeat data points 320, eye tracking data points 330, and brain signal data points 340 are arranged along a temporal dimension. As illustrated, brain signal data points 340 have a higher frequency and smaller power among the four types of biological data points. Brain signal data points 340 might thus be used to align all the data points and to determine the starting timestamp of a sensor event that triggers the identification of one or more key frames. On the other hand, cortisol level data point 310 is the clearest signal indicating that the user is in a particular emotional state, e.g., surprised or stressed, while eye tracking data points 330 anticipate the heartbeat data points 320.

Other types of presentation data have been contemplated. For example, a multi-modal presentation that combines two or more of the key frames 153, audio data corresponding to the key frames, transcription data of the audio data can be generated by the presentation engine 108. Optionally, the multi-modal presentation also includes some of the key biometric data points 155, information derived from the key biometric data points 155, or both.

FIG. 4 is a flow diagram of an example process 400 for providing a presentation based on stored user experience data. For convenience, the process 400 will be described as being performed by a system of one or more processing devices located in one or more locations. For example, a system, e.g., a system that implements the index engine 110 of FIG. 1, appropriately programmed in accordance with this specification, can perform the process 400.

The system receives, from a biometric sensor, a data stream that includes a plurality of biometric data points (step 402). For example, the biometric sensor can be a cortisol level sensor (e.g., an optical cortisol level sensor), a heartbeat sensor, an eye motion sensor (e.g., an eye tracking sensor), a brain signal sensor (e.g., an electroencephalography (EEG) sensor), a galvanic skin response sensor, a temperature sensor, a perspiration sensor (or a sweat sensor), a microphone, a video camera, or the like.

The plurality of biometric data points represent measurements of a particular physiologic characteristic of a user, and in principle, the system can receive a plurality of data streams generated by different biometric sensors. The plurality of data streams include biometric data points that represent measurements of different physiologic characteristics of the same user. Each biometric data point in the data stream is associated with a particular timestamp in a plurality of timestamps. Each timestamp defines a time point at which the corresponding biometric data point is captured by the biometric sensor.

The data stream can be received by the system during presentation of a media content item to the user of a computing device. In some implementations, the computing device is a wearable device that has a display device, e.g., a head mounted display (HMD), that displays the media content item and that includes (or is otherwise coupled to) the biometric sensor. The media content item, which can for example be a movie, a television show, a video clip, or the like, includes a plurality of frames, where each frame is associated with a particular timestamp in a plurality of timestamps. Each timestamp defines a time point at which the corresponding frame is displayed on the computing device. In these implementations, the system can, e.g., by synchronizing the timestamps, associate the biometric sensor data stream with the media content item, such that each biometric data point corresponds to a particular frame in the plurality of frames included in the media content data.

The system determines, based on monitoring the data stream generated by the biometric sensor over a time period during which the media content item is presented for display on the display device, that a particular biometric data point for a particular timestamp in the data stream satisfies a set of one or more predetermined biometric response thresholds (step 404). The system can do this by continuously comparing the biometric data points, i.e., as they become available in a data stream, against the set of predetermined biometric response thresholds. For example, the set of predetermined biometric response thresholds can include different thresholds for different types of biometric sensor data.

In general, the identification of such a sensor event, namely a particular biometric data point satisfying a predetermined biometric response threshold, triggers the identification of one or more key frames from among all of the frames included within the media content item.

In some implementations, the system additionally estimates the emotional states of the user over the presentation time period based on the comparison results. For example, in response to determining that a particular biometric data point satisfies a predetermined biometric response threshold that corresponds to a specific emotional state, the system can detect that the user has transitioned into the specific emotional state. In this way, the transitions in the emotional states of the user can be monitored and continuously tracked. Moreover, a different threshold satisfied by the same biometric data point could result in different key frame(s) to be identified from among all of the frames included within the media content item. This is explained in more detail with reference to FIG. 5, which shows sub-steps 502-506 corresponding to step 404.

Figure 5:
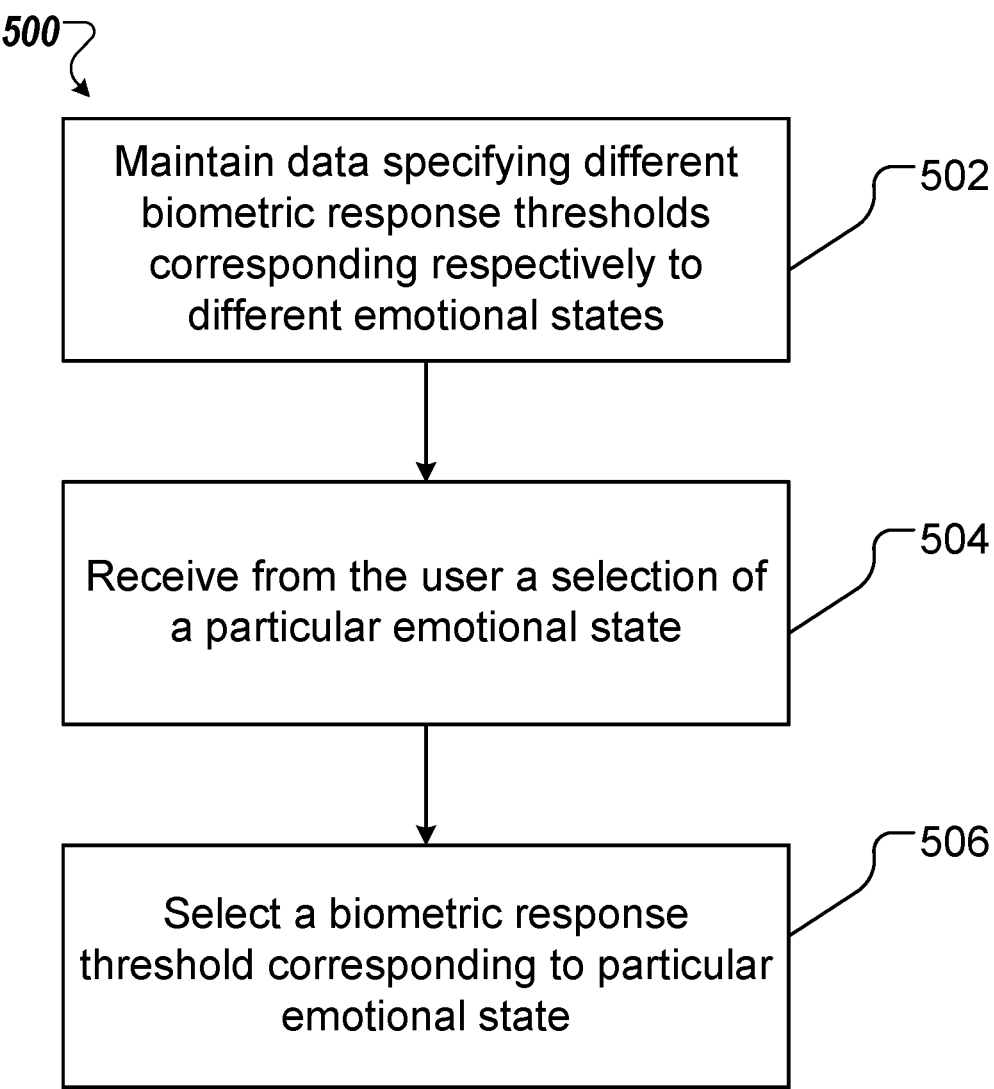
FIG. 5 is a flow diagram of sub-steps of one of the steps of the process of FIG. 4.

FIG. 5 is a flow diagram of sub-steps of one of the steps of the process of FIG. 4.

The system maintains data specifying different biometric response thresholds that correspond respectively to different emotional states (step 502). The emotional states can include neutral, happy, sad, anger, contempt, fear, surprise, confused, stressed, and tender emotions, to name just a few examples. Each emotional state has a corresponding set of one or more biometric response thresholds that are specific to the emotional state.

The system can obtain the biometric response threshold data in any of a variety of ways. For example, the system can receive, e.g., as an upload from a user of the system, manually specified biometric response thresholds. As another example, the system can automatically generate biometric response thresholds based on data determined from evaluation and labeling of biometric sensor data.

The system receives, from the user, a selection of a particular emotional state (step 504). For example, the system can receive the selection through an input device connected to the computing device.

The system selects a set of one or more biometric response thresholds that correspond to particular emotional state as the predetermined biometric response thresholds (step 506). Accordingly, the system compares the biometric data point to the set of one or more predetermined biometric response thresholds that correspond to the particular emotional state (and not to any other thresholds that correspond to different emotional states).

In response to determining that the particular biometric data point satisfies the predetermined biometric response threshold, the system identifies a time period spanning an interval before the identified timestamp through an interval after the identified timestamp (step 406). This time period generally defines a time length of user experience data that should be stored. The time period can, for example, begin at a timestamp that is, e.g., a certain number of antecedent timestamps before the particular timestamp (at which the particular biometric data point in the data stream satisfies the predetermined biometric response threshold), and end at a certain number of precedent timestamps after the particular timestamp. The number of antecedent timestamps need not be the same as that of the precedent timestamps. For example, the number of antecedent timestamps can be greater than the number of precedent timestamps.

Because there are different types of user experience data that can be stored, the system can identify a time period for each of the different types of user experience data. In some implementations, the same time period is identified by the system for the different types of user experience data. In other implementations, however, a different time period is identified for each type of user experience data.

Figure 6:
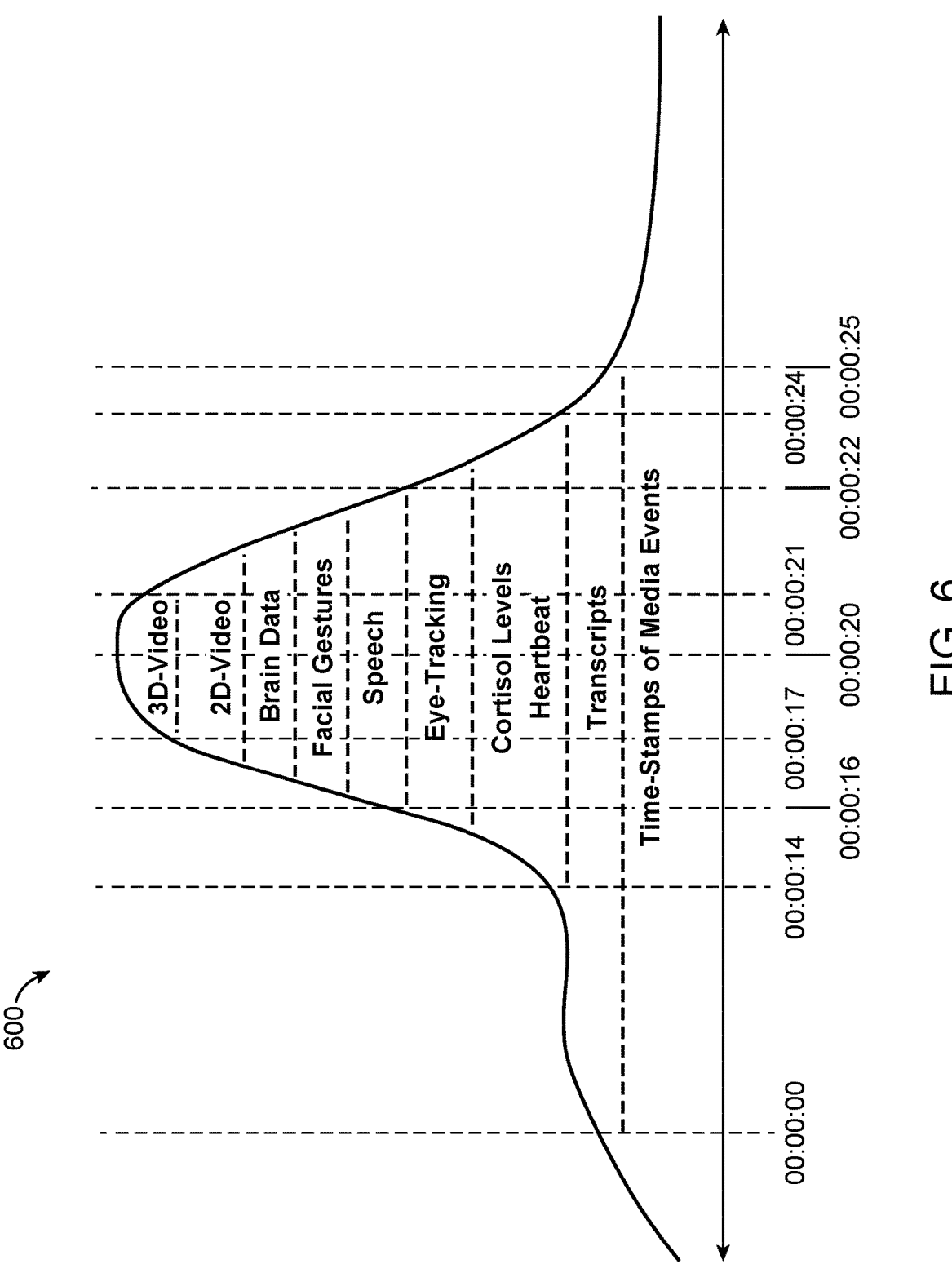
FIG. 6 is an example illustration of identifying different time periods for a particular timestamp.

FIG. 6 is an example illustration of identifying different time periods for a particular timestamp. As illustrated, a video clip is being presented. The presentation of the video clip begins at timestamp 00:00:00, and ends at timestamp 00:00:25. The video clip includes video data, audio data, and transcription data. During the presentation, the system receives multiple data streams generated by a number of biometric sensors and determines, based on monitoring these data streams, that a particular biometric data point for timestamp 00:00:20 in the brain signal data stream satisfies a predetermined biometric response threshold. For example, the threshold can be a threshold that is one of a set of biometric response thresholds that correspond to brain signal sensor data, and that correspond to a surprise emotional state.

In the example of FIG. 6, the system identifies different time periods for different types of user experience data. As illustrated, a time period that lasts a duration of 10 seconds before and after the timestamp 00:00:20 is identified for transcription data. The time period for transcription data begins at timestamp 00:00:14 and lasts until timestamp 00:00:24. A time period that lasts a duration of 4 seconds before and after the timestamp 00:00:20 is identified for 3-D video data. The time period for video data begins at timestamp 00:00:17 and lasts until timestamp 00:00:21.

A time period that lasts a duration of 6 seconds before and after the timestamp 00:00:20 is identified for eye tracking sensor data. The time period for eye tracking sensor data begins at timestamp 00:00:16 and lasts until timestamp 00:00:22. Analogously, time periods in varying durations are identified for brain signal sensor data, facial gesture data, speech data, and cortisol level sensor data.

The system stores user experience data for the identified time period in a user experience data store (step 508). The user experience data store can be implemented in one or more logical or physical storage devices. The user experience data can include (a copy of) a set of key frames in the plurality of frames corresponding to timestamps in the identified time period. As mentioned above, the identified time period spans an interval before the particular timestamp (at which the particular biometric data point in the data stream satisfies the predetermined biometric response threshold) through an interval after the particular timestamp.

In some implementations, as the media content item is being presented for display, the sequence of frames included in the media content item can be temporarily stored in an intermediate buffer to facilitate the subsequent, longer-term storage in the user experience data store. That is, only certain frames that correspond to timestamps within the identified time period are moved from the intermediate buffer to the user experience data store for storage in a persistent manner. Non-key frames that correspond to timestamps outside of the identified time period are not stored in either the intermediate buffer or the user experience data store. e.g., will be discarded from the intermediate buffer.

In the example of FIG. 6, the 3-D video frames that fall within the duration that begins at timestamp 00:00:17 and lasts until timestamp 00:00:21 can be identified as key frames and subsequently stored as (part of) the user experience data. Moreover, the transcripts of the video frames that begin at timestamp 00:00:14 and last until timestamp 00:00:24 can be stored as (part of) the user experience data. Here, both the transcription data and the 2-D/3-D video data are extracted portions of the original video clip that is being presented.

The user experience data can also include (a copy of) a set of key biometric data points corresponding to timestamps in the identified time period.

In the example of FIG. 6, the eye tracking data points that fall within the duration that begins at timestamp 00:00:16 and lasts until timestamp 00:00:22 can be identified as key biometric data points and subsequently stored as (part of) the user experience data. Here, the eye tracking sensor data is captured by an eye tracking sensor. Analogously, other types of biometric sensor data points that fall within the respective durations are stored as (part of) the user experience data. Those data points are captured by different biometric sensors. For example, the facial gesture data points can be captured by a video camera, and the speech data points can be captured by a microphone. Generally, the duration for biometric sensor data that is more data storage intensive, e.g., brain signal sensor data, will be shorter than the duration for biometric sensor data that is less data storage intensive, e.g., heartbeat sensor data.

Returning to FIG. 4, the system generates and provides a presentation based on the stored user experience data (step 410). The system can provide the presentation for display to the same user of the computing device who has viewed the media content item, or another user of a different computing device. For example, the presentation can be in the form of a visual replay, which includes the key frames identified from among all the frames included in the media content item. As another example, the presentation can be in the form of a heatmap, which illustrates a graphical representation of the key biometric data points along a temporal dimension.

Figure 7:
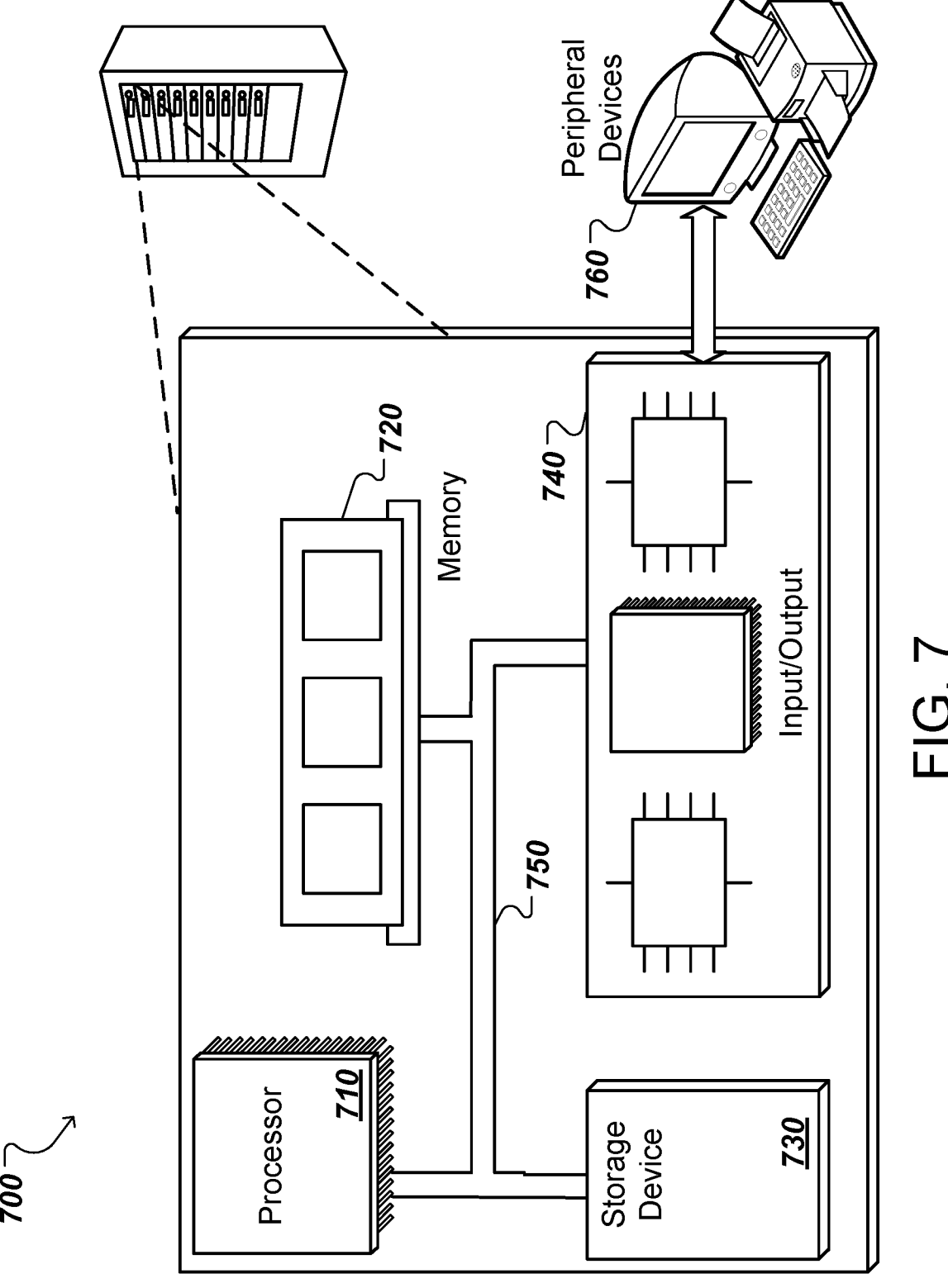
FIG. 7 is a block diagram of an example computer system that can be used to perform operations described herein.

FIG. 7 is a block diagram of an example computer system 700 that can be used to perform operations described above. The system 700 includes a processor 710, a memory 720, a storage device 730, and an input/output device 740. Each of the components 710, 720, 730, and 740 can be interconnected, for example, using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 can include, for example, a hard disk device, an optical disk device, a storage device that is shared over a network by multiple computing devices (e.g., a cloud storage device), or some other large capacity storage device.

The input/output device 740 provides input/output operations for the system 700. In one implementation, the input/output device 740 can include one or more of a network interface devices, e.g., an Ethernet card, a serial communication device, e.g., and RS-232 port, and/or a wireless interface device, e.g., and 802.11 card. In another implementation, the input/output device can include driver devices configured to receive input data and send output data to other devices, e.g., keyboard, printer, display, and other peripheral devices 760. Other implementations, however, can also be used, such as mobile computing devices, mobile communication devices, set-top box television client devices, etc.

Although an example processing system has been described in FIG. 7, implementations of the subject matter and the functional operations described in this specification can be implemented in other types of digital electronic circuitry, or in computer software, firmware, or hardware, including the structures disclosed in this specification and their structural equivalents, or in combinations of one or more of them.

For situations in which the systems discussed here collect and/or use personal information about users, the users may be provided with an opportunity to enable/disable or control programs or features that may collect and/or use personal information (e.g., information about a user's social network, social actions or activities, a user's preferences, or a user's current location). In addition, certain data may be treated in one or more ways before it is stored or used, so that personally identifiable information associated with the user is removed. For example, a user's identity may be anonymized so that the no personally identifiable information can be determined for the user, or a user's geographic location may be generalized where location information is obtained (such as to a city, ZIP code, or state level), so that a particular location of a user cannot be determined.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method comprising:
   receiving, from a biometric sensor associated with a user and during presentation of a plurality of media content frames, a data stream including a plurality of biometric data points wherein each of the plurality biometric data points corresponds to each of a plurality of timestamps, wherein the plurality of timestamps are associated with the plurality of media content frames, and wherein the plurality of biometric data points represent measurements of each of a plurality of physiologic characteristics;

determining, by an index engine, for first timestamp among the plurality of time stamps, a first biometric data point among the plurality of data points in the data stream satisfies a predetermined biometric response threshold;

in response to determining that the first biometric data point satisfies the predetermined biometric response threshold, identifying a time period between a first interval before the first timestamp and a second interval after the first timestamp;

identifying a user experience during the presentation of the plurality of media content frames and storing user experience data corresponding to the identified user experience for the identified time period in a storage device, wherein the user experience data comprises:

a set of key media content frames in the plurality of media content frames corresponding to the plurality of timestamps in the identified time period; and a set of key biometric data points in the plurality of biometric data points, wherein each of the set of key biometric data points corresponds to each of the plurality of timestamps in the identified time period, wherein each of the set of key media content frames is indexed with an index key wherein the index key corresponds to each of the set of key biometric data points; and providing a presentation based on the stored user experience data.

2. The method of claim 1, wherein receiving the data stream comprises:

receiving the data stream while providing the plurality of media content frames to a user in a display of an augmented reality device, a virtual reality device, or a mixed reality device that is equipped with the biometric sensor.

3. The method of claim 1, wherein the presentation of a plurality of media content frames comprises one or more of: two-dimensional video data, three-dimensional video data, or audio data.

4. The method of claim 1, wherein the data stream comprises one of: a cortisol level data stream, a heartbeat data stream, an eye tracking data stream, or a brain signal data stream.

5. The method of claim 1, wherein determining that the first biometric data point satisfies the predetermined biometric response threshold comprises:

assigning different biometric response thresholds to each of the different emotional states;

receiving from the user a selection of a first emotional state among the different emotional states; and selecting a first biometric response threshold among the different biometric response thresholds corresponding to the first emotional state as the predetermined biometric response threshold.

6. The method of claim 5, wherein the predetermined biometric response threshold comprises:

an upper threshold value of the first biometric data point, a lower threshold value of the first biometric data point, or both.

7. The method of claim 1, wherein the user experience data further comprises transcripts of the set of key media content frames.

8. The method of claim 1, wherein the user experience data further comprises facial gesture data, speech data, or both of the user while presenting the plurality of media content frames.

9. The method of claim 1, wherein storing the set of key media content frames in the storage device comprises discarding non-key media content frames in the plurality of media content frames corresponding to timestamps outside of the time period.

10. The method of claim 1, wherein the presentation comprises the stored user experience data, and a biological heat map of the plurality of biometric data points.

11. A system comprising one or more computers and non-transitory computer storage medium for-storing computer readable instructions that are operable, when executed by the one or more computers, to cause the one or more computers to perform operations comprising:

receiving, from a biometric sensor and during presentation of a plurality of media content frames, a data stream including a plurality of biometric data points, wherein each biometric data point corresponds to each of a plurality of timestamps, wherein the plurality of timestamps are associated with the plurality of media content frames, and wherein the plurality of biometric data points represent measurements of a physiologic characteristics;

determining, by an index engine, for a particular first timestamp among the plurality of time stamps, that a particular first biometric data point among the plurality of data points in the data stream satisfies a predetermined biometric response threshold;

in response to determining that the particular first biometric data point satisfies the predetermined biometric response threshold, identifying a time period between a first interval before the particular first timestamp and a second interval after the particular first timestamp;

identifying a user experience during the presentation of the plurality of media content frames and storing user experience data corresponding to the identified user experience for the identified time period in a storage device, wherein the user experience data comprises:

a set of key media content frames in the plurality of media content frames corresponding to the plurality of timestamps in the identified time period; and a set of key biometric data points in the plurality of biometric data points wherein, each of the set of key biometric data points corresponds to each of the plurality of timestamps in the identified time period, wherein each of the set of key media content frames is indexed with an index key wherein the index key corresponds to each of the set of key biometric data points; and providing a presentation based on the stored user experience data.

12. The system of claim 11, wherein receiving the data stream comprises:

receiving the data stream while providing the plurality of media content frames to a user in a display of an augmented reality device, a virtual reality device, or a mixed reality device that is equipped with the biometric sensor.

13. The system of claim 11, wherein the presentation of a plurality of media content frames comprises one or more of: two-dimensional video data, three-dimensional video data, or audio data.

14. The system of claim 11, wherein the data stream comprises one of: a cortisol level data stream, a heartbeat data stream, an eye tracking data stream, or a brain signal data stream.

15. The system of claim 11, wherein determining that the first biometric data point satisfies the predetermined biometric response threshold comprises:

maintaining data assigning different biometric response thresholds corresponding respectively to each of the different emotional states;

receiving from the user a selection of a particular a first emotional state among the different emotional states; and selecting a first biometric response threshold among the different biometric response thresholds corresponding to the first emotional state as the predetermined biometric response threshold.

16. The system of claim 15, wherein the predetermined biometric response threshold comprises:

an upper threshold value of the first biometric data point, a lower threshold value of the first biometric data point, or both.

17. The system of claim 11, wherein the user experience data further comprises transcripts of the set of key media content frames.

18. The system of claim 11, wherein the user experience data further comprises facial gesture data, speech data, or both of the user while presenting the plurality of media content frames.

19. The system of claim 11, wherein storing the set of key media content frames in the storage device comprises discarding non-key media content frames in the plurality of media content frames corresponding to timestamps outside of the time period.

20. A non-transitory computer storage medium encoded with computer readable instructions that, when executed by one or more computers, cause the one or more computers to perform operations comprising:

receiving, from a biometric sensor and during presentation of a plurality of media content frames, a data stream including a plurality of biometric data points, wherein each biometric data point corresponds to each of a plurality of timestamps, wherein the plurality of timestamps are associated with the plurality of media content frames, and wherein the plurality of biometric data points represent measurements of a physiologic characteristics;

determining, by an index engine, for a particular first timestamp among the plurality of time stamps, that a particular first biometric data point among the plurality of data points in the data stream satisfies a predetermined biometric response threshold;

in response to determining that the particular first biometric data point satisfies the predetermined biometric response threshold, identifying a time period between a first interval before the particular first timestamp and a second interval after the particular first timestamp;

identifying a user experience during the presentation of the plurality of media content frames and storing user experience data corresponding to the identified user experience for the identified time period in a storage device, wherein the user experience data comprises:

a set of key media content frames in the plurality of media content frames corresponds corresponding to the plurality of timestamps in the identified time period; and a set of key biometric data points in the plurality of biometric data points wherein, each of the set of key biometric data points corresponds to each of the plurality of timestamps in the identified time period, wherein each of the set of key media content frames is indexed with an index key wherein the index key corresponds to each of the set of key biometric data points; and providing a presentation based on the stored user experience data.

* * * * *